United States Patent [19]

Zimmon

[11] Patent Number: 5,782,747
[45] Date of Patent: Jul. 21, 1998

[54] SPRING BASED MULTI-PURPOSE MEDICAL INSTRUMENT

[75] Inventor: David S. Zimmon, Port Washington, N.Y.

[73] Assignee: Zimmon Science Corporation, Port Washington, N.Y.

[21] Appl. No.: 635,766

[22] Filed: Apr. 22, 1996

[51] Int. Cl.⁶ .................................................. A61B 1/00
[52] U.S. Cl. .......................... 600/104; 600/101; 606/205
[58] Field of Search ............................. 600/101, 104, 600/106, 107; 606/205, 206, 207, 208, 113, 170, 106, 144, 148, 171, 139, 140, 141, 142, 151

[56] References Cited

U.S. PATENT DOCUMENTS

| | | |
|---|---|---|
| 1,284,060 | 11/1918 | Culman . |
| 3,404,677 | 10/1968 | Springer . |
| 3,858,586 | 1/1975 | Lesen ............................ 600/104 X |
| 4,103,680 | 8/1978 | Yoon ............................. 600/104 |
| 4,174,715 | 11/1979 | Hasson . |
| 4,222,380 | 9/1980 | Terayama ....................... 600/104 X |
| 4,257,420 | 3/1981 | Terayama ....................... 600/104 X |
| 4,427,014 | 1/1984 | Bel et al. . |
| 4,655,219 | 4/1987 | Petruzzi . |
| 5,172,700 | 12/1992 | Bencini et al. . |
| 5,222,973 | 6/1993 | Sharpe et al. . |
| 5,304,183 | 4/1994 | Gourlay et al. ................. 606/205 X |

*Primary Examiner*—Beverly M. Flanagan
*Attorney, Agent, or Firm*—Woodard, Emhardt, Naughton Moriarty & McNett

[57] ABSTRACT

A spring based multi-purpose medical instrument having an internal guiding structure and a slotted end cap. The instrument being deployable through a catheter or endoscope and further passable within the human anatomy. The slotted end cap and internal guiding structure providing for precise controlled movement of the spring jaws through a remote actuator. Further, the slotted end cap preventing the loss of the spring jaws within the internal body cavity upon separation from the actuator. In another embodiment of the spring based multi-purpose instrument the jaws being rotatable for cutting and fragmenting materials.

47 Claims, 7 Drawing Sheets

SPRING BASED MULTI-PURPOSE MEDICAL INSTRUMENT

BACKGROUND OF THE INVENTION

The present invention relates generally to the design and construction of a multi-purpose medical instrument for performing procedures at a distance from the operator. More particularly, the present invention has one embodiment wherein a remotely controllable spring jaw for grasping and/or cutting is guided and controlled by a jaw guiding structure and an end cap having apertures therein. The jaw guiding structure and end cap allow precise movement of the spring jaws at a distance from the operator. Although, the present invention was developed for medical procedures, certain applications may be outside of this field.

The development of flexible endoscopic instruments has made possible minimally invasive surgical operation on many remote regions within a patient. Examples of such regions within the human body applicable for minimally invasive surgical operations include body cavities of the brain, chest, abdomen, spine, joints, eye, ear and sinuses as well as blood vessels, pancreatic duct, bile duct, urethra and ureter in the urinary tract, lungs, and the gastrointestinal system. Various surgical and manipulative instruments have been developed for use in association with endoscopes to perform surgical procedures, obtain biopsies, grasp foreign objects, cut tissue and appliances, and for the removal of obstructive deposits within the patient. These types of accessories provide alternatives to the more traditional, and decidedly more traumatic, invasive surgical procedures requiring disassembly or traditional open surgical incision to accomplish their goals.

Medical practitioners utilize instruments deployable through a deployment device, such as a catheter or endoscope, to perform grasping and cutting operations at remote sites within the patient. Generally, the prior instruments have included a fulcrom scissor jaw or blades which are activated by a cable or push/pull wire. Prior medical instrument designers have been limited by the respective size and diameter passable through a lumen in the deployment device, and ultimately by the size of a body entrance site or passage through which the device passes.

A limitation associated generally with the prior art instruments has been the resistance developed between the internal pull wire and the outer tube of the device upon actuation of the jaw fulcrum. The resistance between the outer tube and the internal pull wire increases with the fourth power of the curve radius that the device traverses. In order to withstand the increased pull necessary to actuate the jaw of a device passing through a cavity having a plurality of curves, the outer tube must be stiffened. By increasing the stiffness of the outer tube the maneuverability of the device is severely limited. Further, the maneuverability limitation is compound during procedures requiring increased force, such as to crush a stone, grasp and firmly hold a foreign body for removal, or cut through a tough tissue, suture or wire.

Another limitation associated with many prior art instruments is manifested when retrieving an object. Retrieval of an object requires straightening of the deployment device, and the retrieval instrument. During the straightening of the retrieval instrument the relative geometry of the retrieval instrument's actuating cable and outer tube are changed. Subsequent to straightening the retrieval instrument it is often necessary to increase the pull on the actuator cable to maintain a satisfactory jaw closure. Subjecting the retrieval instrument to this increased pull often causes the outer tube to collapse, the actuating cable to break and/or bind, and the jaws to distort.

A practitioners relaxation of the actuator cable tension in order to prevent binding within the tube or damaging tissue may allow the release of the grasped object into the internal cavity. Similarly to exert greater force on the fulcrum scissor jaws via the actuator cable often forces the outer tube to curve moving the jaws away from the object. The requisite complex maneuvering associated with using many of the prior art devices is a great disability since it requires close coordination between the endoscopist and a second operator who is required to operate the instrument, thereby rendering the operation difficult and subject to failure.

Another limitation associated with many prior art devices is during operation there is uncontrolled movement both within the deployment device or pathway and at the end of the instrument thereby preventing the precise closure often necessary for grasping or crushing. The irregular binding movement creates friction and wear within the instrument, which often compounds thereby causing instrument failure.

Although the prior art apparatus are steps in the right direction, the need for additional improvements still remains. The present invention satisfies this need in a novel and unobvious way.

SUMMARY OF THE INVENTION

One embodiment of the present invention contemplates an instrument for performing a medical procedure. The apparatus comprises: an elongated flexible member having an aperture extending longitudinally therethrough, the member having a proximal end and an opposite distal end; an actuator positioned within the aperture, the actuator having a proximal end and an opposite distal end; a spring jaw connected to the distal end of the actuator, the jaw being deployable remotely for performing a medical procedure; and an internal jaw guide at the distal end of the member, the jaw guide contacting along the jaw for controlling the precise movement of the jaw, the jaw guide defining a cavity within the member for receiving a substantial portion of the jaw therein.

One object of the present invention is to provide an improved spring based multi-purpose medical instrument.

Related objects and advantages of the present invention will be apparent from the following description.

DESCRIPTION OF THE PREFERRED EMBODIMENT

Figure 1:
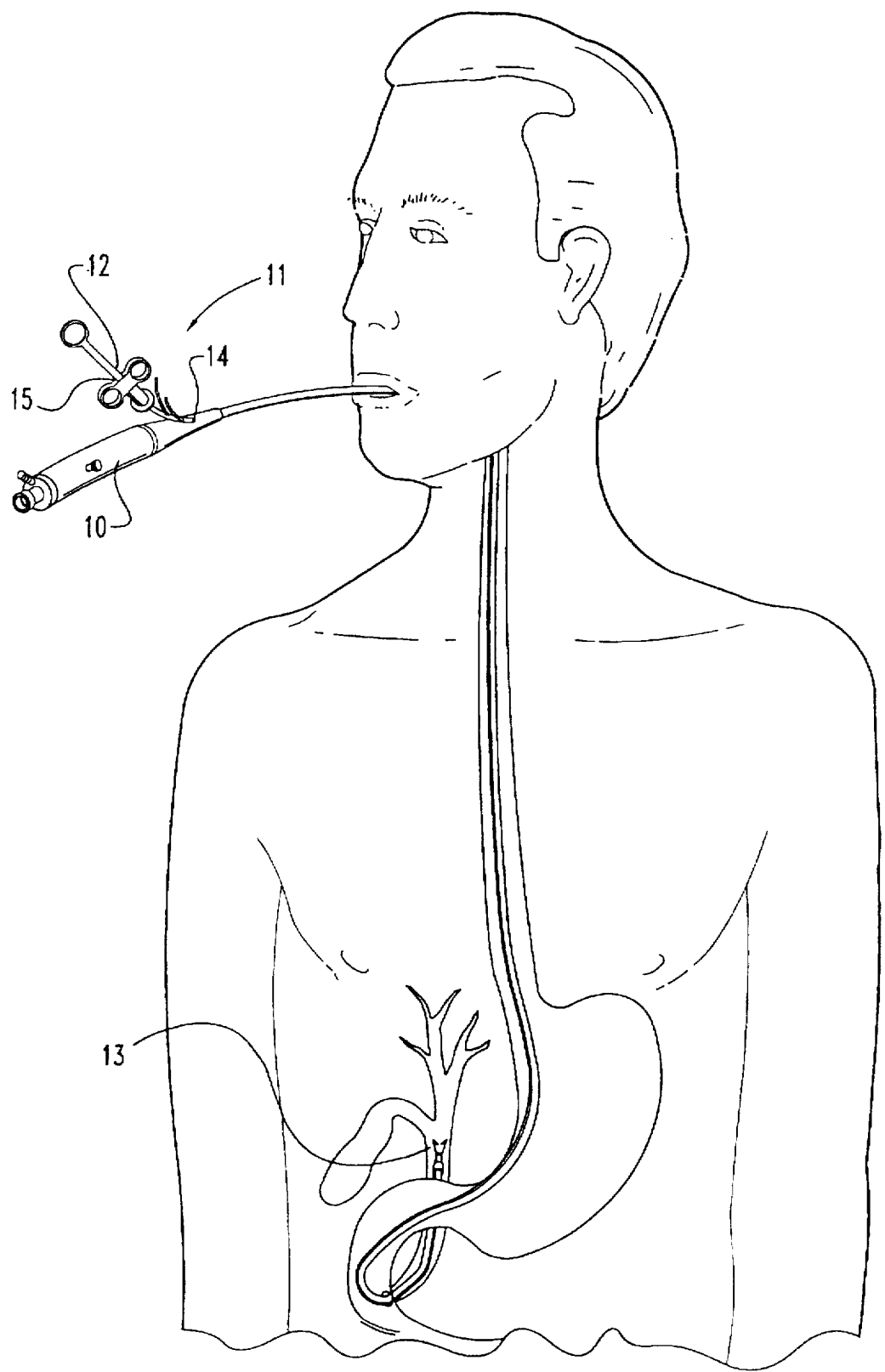
FIG. 1 is a perspective view of one embodiment of the spring based multi-purpose medical instrument positioned within a patient.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

With reference to FIG. 1, there is illustrated a patient having an endoscope 10 passing through the oral cavity, esophagus, stomach, and into the bile duct. Methods of passing an endoscope 10 within a patient are generally known to those skilled in the art. A multi-purpose spring jaw medical instrument 11 is deployable through a lumen 14 extending within the endoscope. Endoscopes having lumens for the passage of auxiliary instruments are generally known to those having ordinary skill in the art, and have a variety of lengths. It is preferred that the endoscope have a length of at least two hundred centimeters. The lumen 14 within the endoscope preferably has a diameter of about 4.0 millimeters.

Further, it is preferred that the lumen have a diameter in the range of about 1.5 to 4.0 millimeters. Other lumen 14 sizes are contemplated herein that will allow the ready passage of the multi-purpose spring jaw medical instrument 11 therethrough. Deployment of the multi-purpose spring jaw medical instrument 11 can also be accomplished through a catheter positioned within the patient, wherein the catheter has substantially similar lumen characteristics as the endoscope. Further, other techniques of deployment known to those skilled in the art are contemplated herein.

The multi-purpose spring jaw medical instrument 11 has a proximal end 12, external to the patient, and a distal end 13 positionable within a body cavity. While the distal end 13 of the instrument 11 is illustrated within the bile duct, it is understood that the instrument 11 is deployable into other regions within the patient, such as: the brain, chest, abdomen, stomach, spine, joints, eyes, ear and sinuses as well as blood vessels, pancreatic duct, uretha and urether in the urinary tract, lungs and the gastrointestinal system.

Figure 2A:
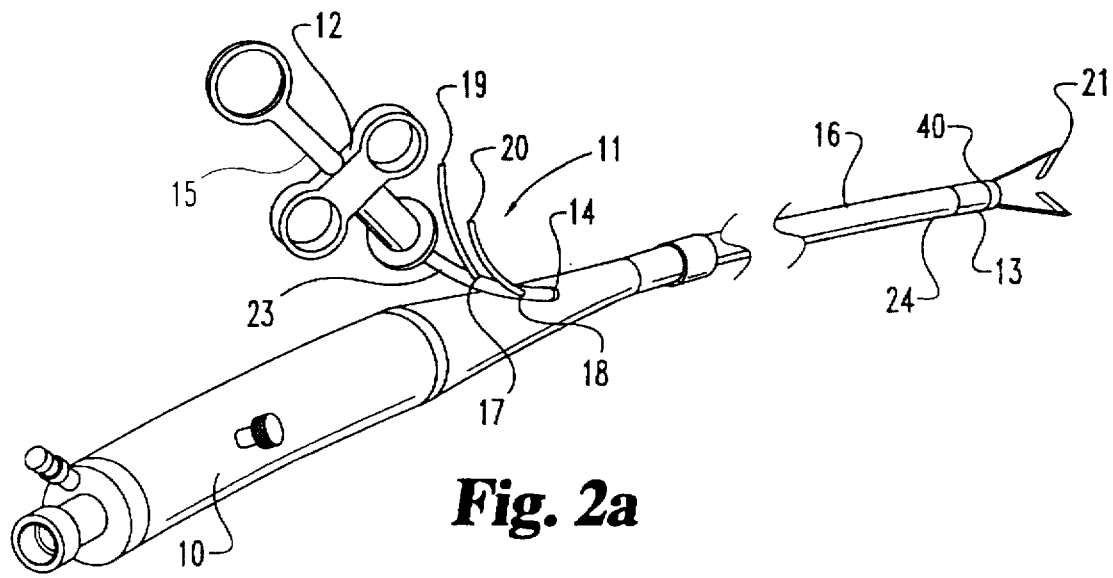
FIG. 2a is a perspective view of the spring based multi-purpose medical instrument of FIG. 1, passing through an endoscope.

With reference to FIG. 2a, there is illustrated the multi-purpose spring jaw instrument 11 positioned within the lumen 14 of the endoscope 10 and removed from the patient. Instrument 11 includes a proximal end 12 and an opposite other distal end 13. The proximal end 12 has a handle 15 for a medical practitioner to manipulate in order to control the relative movement of the instrument 11. An elongated outer tube 16 forms a portion of instrument 11 and is disposed in close sliding contact with the surface defining lumen 14 and extends from the proximal end 12 to the distal end 13 of instrument 11. The tube 16 has a plurality of ports therein for the utilization of luminal catheter techniques. In one embodiment the plurality of ports include a pair of ports 17 and 18 that receive tubes 19 and 20 therethrough and into the instrument 11. The luminal catheter techniques utilized in association with tubes 19 and 20 are for the irrigation and aspiration of contents from within an internal body cavity. Further, luminal catheter techniques utilized through the instrument include, but are not intended to be limited to, the injection of a contrast solution and the sampling of fluid from within the patient. In another embodiment the application of cautery or electric current is done through a shaft connecting to an operating head/jaw of the instrument 11. The electric current or cautery may be passed through one of said plurality of lumens. Further, the transmission of signals through the instrument allows for monitoring of event changes.

A spring jaw 21 is located at the distal end 13 of the instrument 11. A variety of spring jaw designs are contemplated herein for incorporation into the spring based multi-purpose instrument 11; such as jaw designs for grasping, cutting, and retrieving. One of a litany of advantages associated with the multi-purpose spring jaw instrument 11 is that it allows for a relatively small diameter tube 16 to deliver a jaw 21 having a wide interjaw distance. The instrument 11 is capable of utilizing spring jaws having an opening in the range of about 2–20 millimeters. One form of the spring jaw 21 having a jaw opening of about 2–3 millimeters, and another form of the spring jaw 21 having an opening of about 15–20 millimeters. The smaller jaw opening being suited for narrow fragile structures, while the larger jaw opening being suited for activities such as the grasping of stones and polyps. However, a wide variety of jaw sizes are contemplated herein and are deployable through tube 14.

Figure 2B:
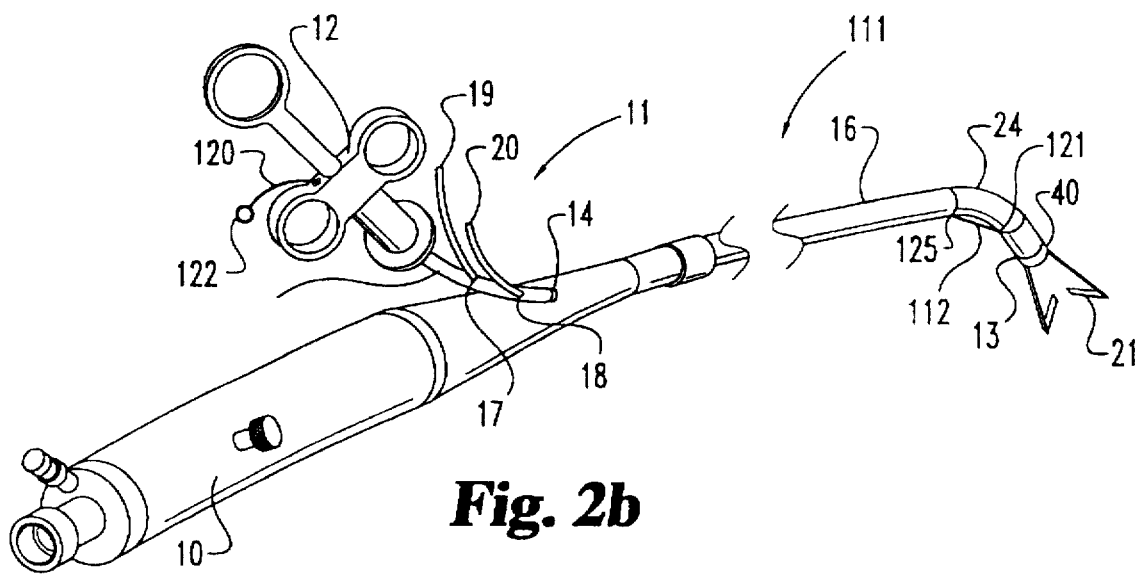
FIG. 2b is a perspective view of another embodiment of the spring based multi-purpose medical instrument having a deflection wire, the deflection being shown exaggerated.

With reference to FIG. 2b, there is illustrated a multi-purpose spring based instrument 111 that is substantially similar to instrument 11. It is understood that like reference numerals refer to like features between the two instruments. Instrument 111 adds a deflection actuator 112 for allowing the practitioner to remotely deflect the distal end 13 of the instrument. The deflection of the distal end 13 has been shown in an exaggerated fashion. Deflection actuator 112 has a proximal end 120 and an opposite other distal end 121. Positioned at the proximal end 120 is a handle 122 for grasping by the practitioner. The deflection actuator 112 passing through one of the plurality of lumens within the outer tube 16. At a location near the distal end 13 an aperture 125 allows the passage of the deflection actuator along the outer surface of tube 16. It is understood that instrument 111 would have its outer tube 16 formed of a soft flexible material. Other methods remotely controlling the deflection of the distal end 13 of the instrument are contemplated herein.

Figure 3:
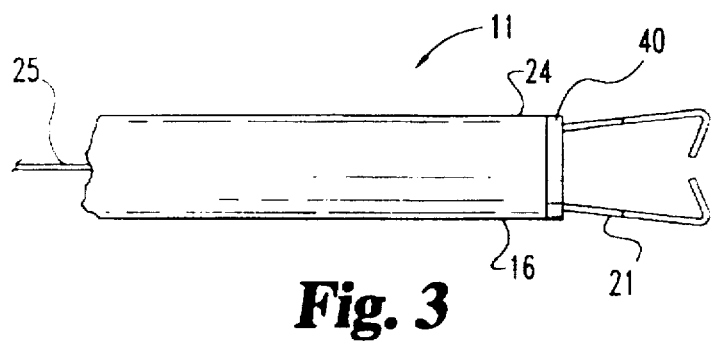
FIG. 3 is a partial side elevational view of the distal end of the FIG. 2a spring based multi-purpose medical instrument.

Referring to FIG. 3, there is illustrated a partial side elevational view of instrument 11. In the preferred embodiment the elongated outer tube 16 is substantially cylindrical and has a central aperture 60 (FIG. 5) extending longitudinally therethrough. The outer tube 16 having a proximal end 23 and an opposite operative distal end 24. Flexible tube 16 is preferably formed of a material compatible with human tissue and bodily fluids. In one embodiment suitable for deployment through an endoscope the outer tube 16 is formed of plastic. In an alternative embodiment suitable for percutaneous use the outer tube is formed of metal. However, other materials are contemplated herein provided that they meet the operating characteristics necessary for instrument 11. Thus, it is understood that depending upon the specific application the outer tube 16 is formed of materials having characteristics that give the tube relative properties including, but not limited to being soft and flexible or hard and more rigid.

A jaw actuator 25 is moveably positioned within the outer tube 16. The jaw actuator 25 having a relatively thin diameter and being slideable within the central aperture. In a preferred embodiment the actuator 25 is a very thin wire, however other embodiments contemplate plastic, metal and composite structures. In a preferred embodiment the actuator 26 has a diameter of 0.36 mm, however it is understood that other diameter sizes are contemplated herein. The actuator includes a proximal end 26 and an opposite distal end 27. Proximal end 26 being connected to the instrument handle 15 and located external to the patient's body. Distal end 27 located within the outer tube 16 and proximate the distal end 24 of tube 16. In the preferred embodiment the actuator 25 has a length measured from the proximal end 26 to the distal end 27, that is less than the measured length of the outer tube 16 extending from proximal end 23 to distal end 24. The relative difference in length of the actuator 25 and the outer tube 16 prevents the jaw 21 from being fully positioned outside of the instrument 11.

Figure 4:
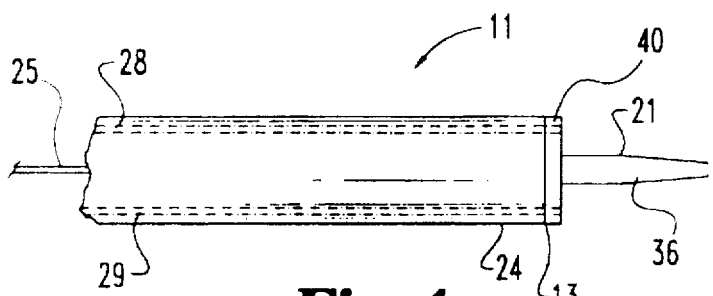
FIG. 4 is a side elevational view of the distal end of the FIG. 2a spring based multi-purpose medical instrument rotated 90° and showing two lumens therethrough as hidden lines.

Referring to FIG. 4, there is illustrated the distal operating end 13 of the instrument 11 having been rotated about 90 degrees. One form of the present invention includes a plurality of isolated lumens extend longitudinally through the outer tube 16. In a preferred embodiment a pair of lumens 28 and 29 are formed in the body of the outer tube 16, traverse the length of tube 16, and are located 180 degrees apart and positioned between the arms 36 and 37 of jaws 21. The plurality of lumens allow for the deployment of luminal catheter techniques as set forth herein, and as known to those of ordinary skill in the art. In the preferred embodiment the lumens 28 and 29 are in fluid communication with tubes 19 and 20. One of the lumens being for the aspiration of the contents from a body cavity, while another lumen being for irrigation or radiopaque contrast. Further, the spring based multi-purpose instrument 11 can be formed with no auxiliary lumens, such as lumens 28 and 29, or with a plurality of auxiliary lumens. Preferably the outer tube 16 is formed as an extruded plastic tube with a plurality of integral lumens. The lumens being isolated from one another so as to prevent the mixing of fluids flowing in the plurality of lumens.

Figure 5A:
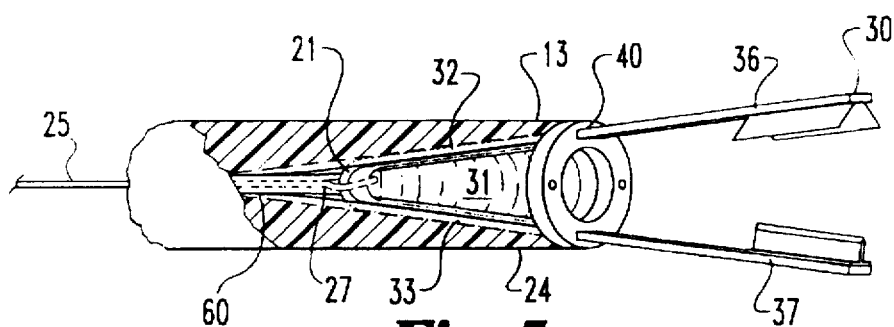
FIG. 5a is a partial sectional view of another embodiment of the spring based multi-purpose medical instrument.

With reference to FIG. 5a, there is illustrated a partial sectional view of the distal end 13 of instrument 11 with a cutting/operating head 30. It is understood that operating heads, such as cutting head 30, are many and varied and that their selection depends upon the medical procedure to be performed by the medical practitioner. Many of the cutting/operating/grasping heads disclosed herein being deployable over a guide wire. The wire guide passing through an aperture formed in the jaw 21. The illustration of different cutting and grasping heads in conjunction with spring jaw 21 is not intended to be limiting to the rest of instrument 11.

When spring jaw 21 is in a retracted position a substantial portion of the spring jaw 21 is located within a cavity 31. The cavity 31 being located at the distal end 24 of the outer tube 16. In one form of the present invention the cavity 31 defines a slot having a cavity upper surface 32 and a cavity lower surface 33 that engage and contact surfaces of the spring jaw 21. The cavity upper and lower contact surfaces 32 and 33 form an internal jaw guide which functions to support and guide the spring jaw 21. In the preferred embodiment the cavity 31 is a slot having a substantially v-shape formed in the distal end 24 of the outer tube 16. In another embodiment of instrument 11 the cavity 31 is formed as part of a separate piece that is attached to the tube 16. The internal guide structure is designed and manufactured to contact along the spring jaw 21 for controlling the precise movement of the jaw. Alternative embodiments contemplate internal jaw guiding structures of different geometric forms.

Figure 5B:
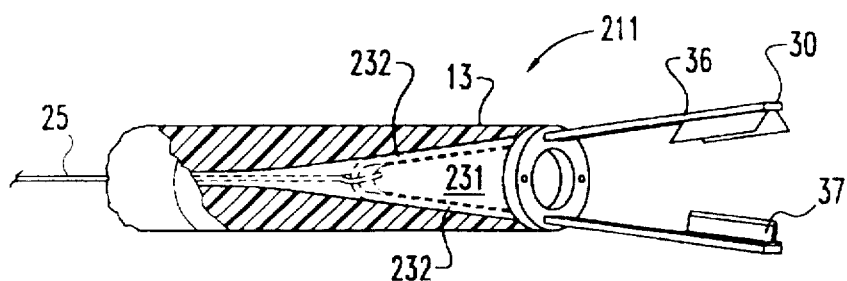
FIG. 5b is a partial sectional view of one embodiment of the spring based multi-purpose mechanical instrument having a conical internal jaw guide.

With reference to FIG. 5b, there is illustrated a partial sectional view of the distal end 13 of an instrument 211 with cutting/operating head 30. It is understood that instrument 211 is substantially similar to instrument 11 and like reference numerals indicate like features. The primary distinction between the two instruments is that spring jaw 31 is located in a conical cavity 231. The conical cavity 231 having a contacting surface 232 that engages the surface of the spring jaw 21. The conical surface 232 functioning to support the spring jaw 21. Other geometric forms for cavity 231 are contemplated herein.

Figure 6:
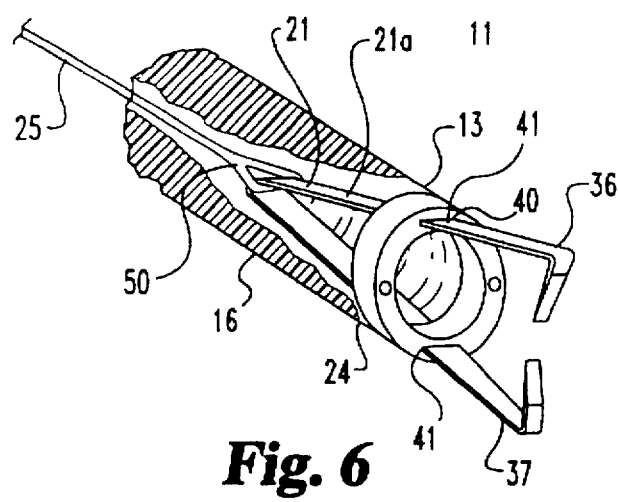
FIG. 6 is a partial sectional view of another embodiment of the spring based multi-purpose medical instrument.

With reference to FIG. 6, there is illustrated a perspective view in partial section of the distal end 13 of instrument 11; the instrument 11 having another operating head connected thereon. For clarity, the tube structure 16 proximate the actuator 25 has been removed to allow a fuller discussion of the connection between the actuator 25 and the spring jaw 21. However, it is understood that in the preferred embodiment of instrument 11 the actuator 25 is in close sliding contact with the surface forming a central aperture 60 (FIG. 7) that extends longitudinally through the tube 16. The actuator 25 being in a close sliding fit with aperture 60 in order to minimize play or slop therebetween.

One embodiment of instrument 11 utilizes a loop 50 formed of the actuator to connect around the spring jaw 21 to connect them together. The loop 50 being secured by techniques known to persons of ordinary skill in the art such as mechanical affixation, the use of adhesive, brazing, welding, clamps, etc. The connection of the actuator 25 to the spring jaw 21 is guided by the desire to have a flexible joint. The use of a flexible jaw body 21a and a flexible connection between the actuator 25 and the spring jaw 21 allows for reduced resistance in passing the instrument 11 through a lumen having a multitude of curves and angles. Further, the jaw 21 is deployable remotely and operable at a region or site within the patient at a distance from the entry point.

Figure 7A:
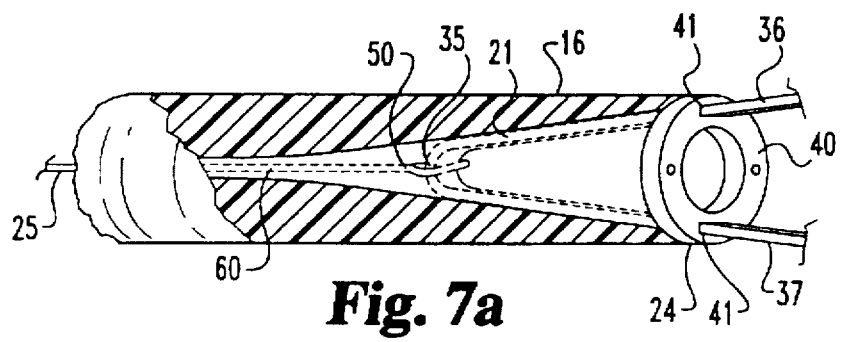
FIG. 7a is an enlarged partial side elevational sectional view of the spring based multi-purpose medical instrument of FIG. 3 showing the jaw actuator connected to the jaws by a loop.
Figure 7B:
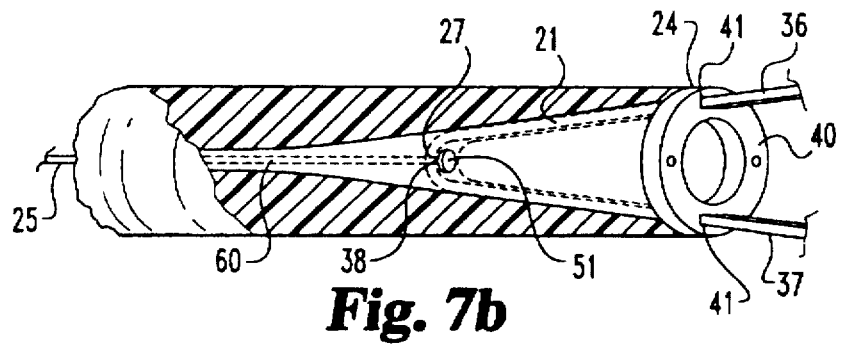
FIG. 7b is an enlarged partial side elevational view of another embodiment of the spring based multi-purpose medical instrument having the jaw actuator connected to the jaw by a retaining button.

With reference to FIGS. 7a and 7b, there are illustrated attachment structures for connecting the actuator 25 to the spring jaw 21. More particularly in FIG. 7a, there is illustrated the loop 50 connection. In the preferred embodiment the spring jaw 21 has an apex 35 and a pair of spaced arms 36 and 37 originating from the apex. The loop 50 passing around the apex 35 of the jaw 21 to connect the components together. Referring to FIG. 7b, there is illustrated an alternative connection structure utilizing an enlarged head 51 that is connected to the distal end 27 of the actuator 25. An aperture 38 being formed through the spring jaw 21 proximate the apex 35 for the passage of the actuator 21. The enlarged head 51 bearing upon the body of the spring jaw 21 to retain the actuator 25 connected to the jaw 21. In the preferred embodiment the enlarged head 51 is a rivet connected to the actuator 25. Other mechanical affixation techniques generally known to those skilled in the art are contemplated herein.

With reference to FIGS. 1-7, there is illustrated an end cap 40 that is positioned around the distal end 24 of outer tube 16. The end cap is fixedly attached to the distal end 24 of outer tube 16. In the preferred embodiment the end cap 40 stabilizes the distal end 24 of the flexible tube 16 and guides jaws 21. It is preferred that the end cap be formed of metal having a relatively thin wall. End cap 40 having a spring guiding structure formed therein, and in the preferred embodiment the spring guiding structure comprises a pair of spaced slots 41. In one embodiment the spaced slots 41 being spaced 180 degrees apart and having a shape corresponding to the cross section of the spring arms 36 and 37. The end cap 40 further functioning to minimize or eliminate twisting and/or lateral movement of the spring arms 36 and 37 which prevents misalignment of the jaws. The spacing and geometric configuration of the slots 41 formed in the end cap allows for precision spacing between the jaws 21. The end cap 40 adds a safety feature in that it prevents loss of the spring jaw 21 if the actuator 25 should become separated from the spring jaw.

The spring jaw 21 is preferably formed of a single strip of material having a desired spring constant. Material selection appropriate for the spring jaws 21 includes, but is not limited to, plastics, polymers and spring steels. In the preferred embodiment the spring jaw 21 is formed of a substantially flat spring steel that is folded in the center to form a substantially v-shape. In alternative embodiment jaws formed with living hinges, composite steel and spring steel, composite plastic and steel are contemplated. In a more preferred embodiment the spring jaw 21 is formed of nitinol.

The actuator 25 is disposed within the outer tube 16 and are both connected at their proximal end to handle 15. Practitioners can manipulate both the actuator 15 and the outer tube 16 at this remote handle 15. In one embodiment (FIG. 2b) at least a portion of the outer tube 16 being deflectable and controllable upon the practitioner manipulating the proximal end 120 of the deflection actuator 112, thereby giving the instrument deflection capability though a single actuator. Further, the jaw 21 is opened and closed by the relative movement between the outer tube 16 and the actuator 25. The practitioner is given the operating flexibility to manipulate either the outer tube or the actuator to move the jaws 21.

Figure 8:
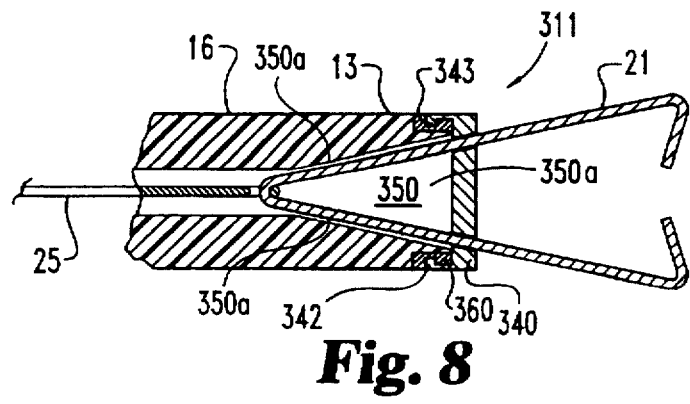
FIG. 8 is a partial sectional view of another embodiment of the spring based multi-purpose mechanical instrument having a rotatable spring jaw.

With reference to FIG. 8, there is illustrated a partial sectional view of another embodiment of the mechanical spring based instrument. Instrument 311 being substantially identical to instrument 11 and like reference numerals indicating like elements. Instrument 311 having at its distal end 13 a rotatable spring jaw 21 for cutting and/or fragmenting material. A cavity 350 being formed in the tube 16 to allow the spring jaws 21 to rotate. The cavity having a bearing surface 350a that supports and allows the rotation of the jaws thereon. In the preferred embodiment the cavity has a substantially conical shape, however other geometric forms are contemplated herein. The spring jaw 21 passing through a rotatable end cap 340 that rotates about the distal end 13 of tube 16. The end cap 340 being captioned and rotatable on the tube 16. In one embodiment an upstanding lip 342 seats in a circumferential groove 343 formed in a bearing cap 360 to retain the end cap 340 on the tube 16. The bearing cap 360 being fixedly secured to the tube 16. The mating surfaces of the end cap 340 and the bearing cap 360 forming corresponding bearing surfaces to allow the smooth rotation of spring jaws 21. Actuator 25 being rotatable and having sufficient rigidity to allow the substantial transmission of rotary motion therethrough to effectuate rotating the end cap 340 and spring jaws 21.

Figure 9A:
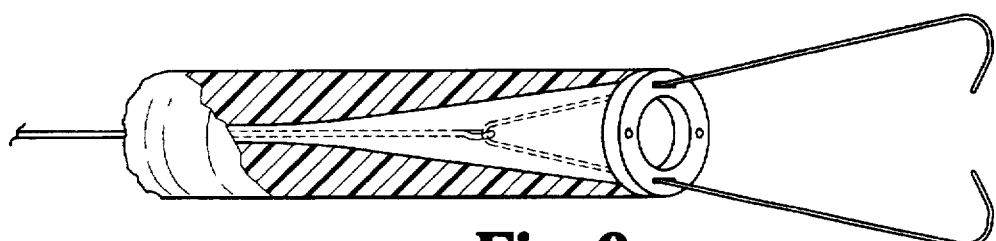
FIG. 9a is another embodiment of the spring based multi-purpose medical instrument having an open loop locking jaw.
Figure 9B:
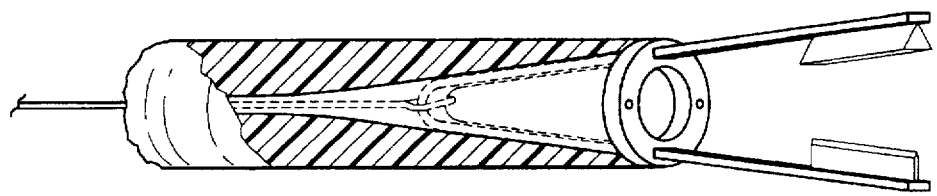
FIG. 9b is another embodiment of the spring based multi-purpose medical instrument having an anvil cutting jaw.
Figure 9C:
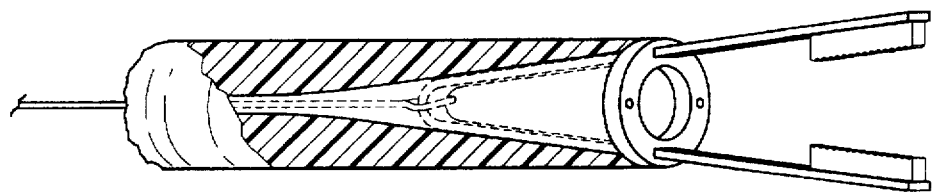
FIG. 9c is another embodiment of the spring based multi-purpose medical instrument having a serrated jaw.
Figure 9D:
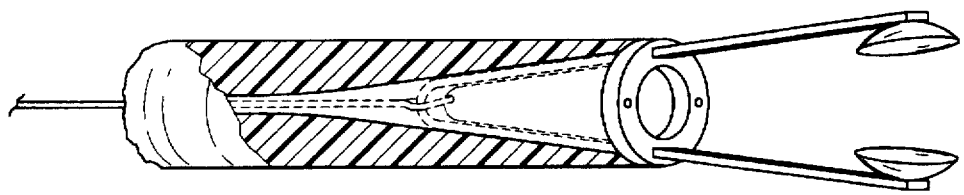
FIG. 9d is another embodiment of the spring based multi-purpose medical instrument having a cup biopsy jaw.
Figure 9E:
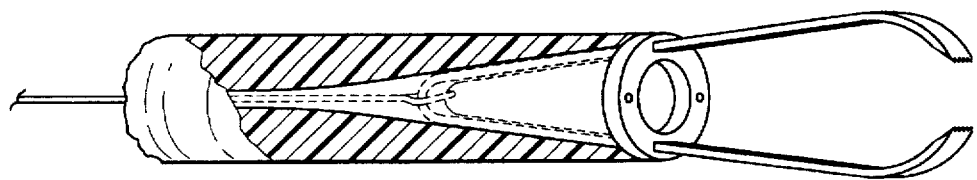
FIG. 9e is another embodiment of the spring based multi-purpose medical instrument having a distal grasping jaw.
Figure 9F:
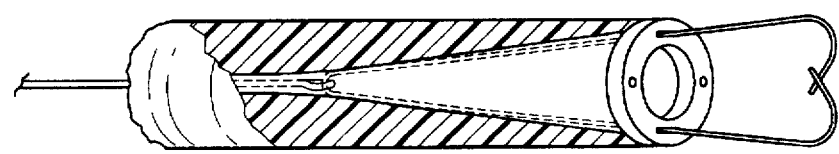
FIG. 9f is another embodiment of the spring based multi-purpose medical instrument having a closed loop locking jaw.
Figure 9G:
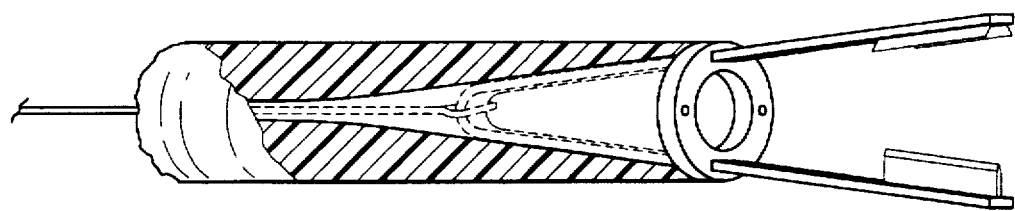
FIG. 9g is another embodiment of the spring based multi-purpose medical instrument having a cutting jaw.
Figure 9H:
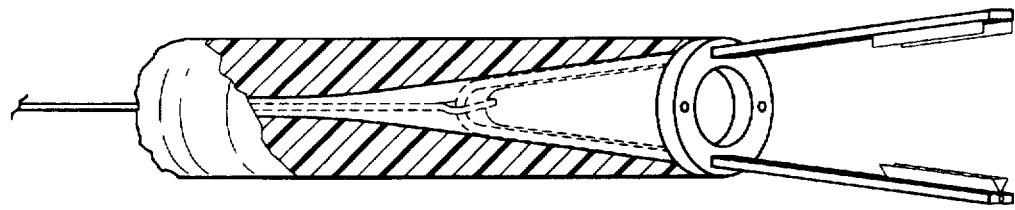
FIG. 9h is another embodiment of the spring based multi-purpose medical instrument having a deep cutting biopsy jaw.
Figure 10A:
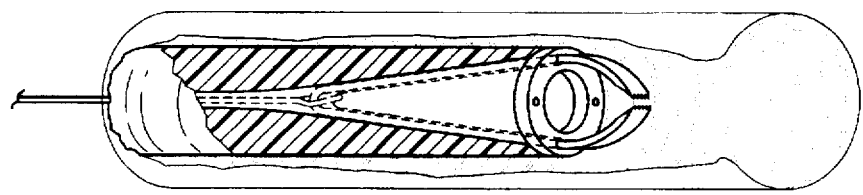
FIG. 10a is an illustrative view of one embodiment of the spring based multi-purpose medical instrument in a retracted position within a lumen inside the patient.
Figure 10B:
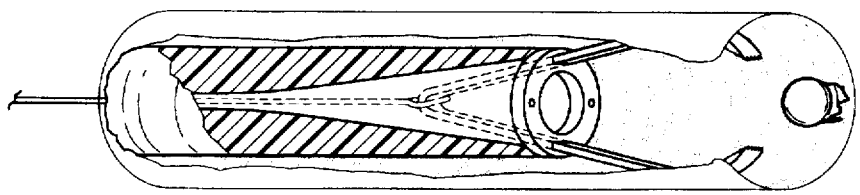
FIG. 10b is an illustrative view of the FIG. 9a spring based multi-purpose medical instrument wherein the jaws have been extended to reach for an object.
Figure 10C:
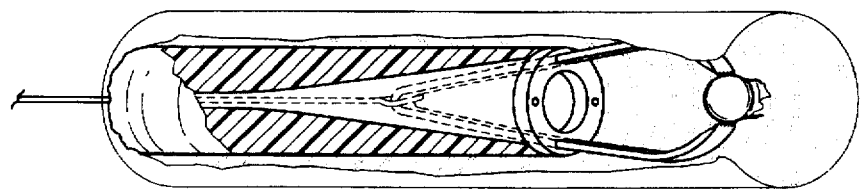
FIG. 10c is an illustrative view of the FIG. 9a spring based multi-purpose medical instrument wherein the jaws have contacted the object.
Figure 10D:
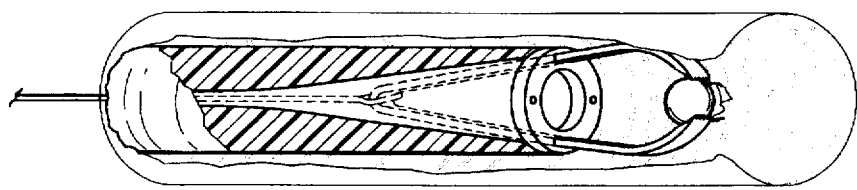
FIG. 10d is an illustrative view of the FIG. 9a spring based multi-purpose medical instrument wherein the jaws have captured the object.
Figure 10E:
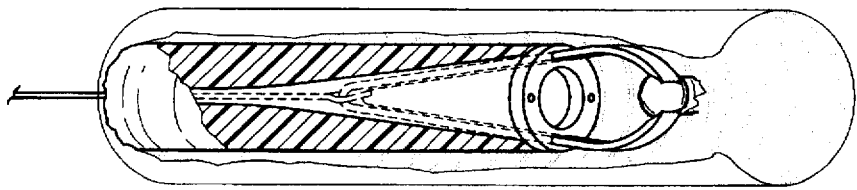
FIG. 10e is an illustrative view of the FIG. 9a spring based multi-purpose medical instrument wherein the jaws have been retracted after capturing the object.

With reference to FIGS. 9a-9h, there are illustrated a multitude of operating heads disposed on jaws 21 of the instrument 11. The operating heads may be formed integral with the jaws 21, or be a separate piece connected thereto. It is understood that the operating heads are representative of the flexibility of the instrument and are not intended to be limiting in any fashion. More particularly in FIG. 9a, there is illustrated an open loop jaw design suitable for grasping a object. With reference to FIG. 9b, there is illustrated a cutting jaw having a knife edge and an opposite anvil. The jaw structure in FIG. 9c, comprises a pair of opposing serrated surfaces for grasping and/or crushing an object. Referring to FIG. 9d, there is illustrated a cup biopsy jaw that is useful for obtaining a tissue sample. The grasping device in FIG. 9e, has a pair of opposing jaws with distal serrations thereon. With reference to FIG. 9f, there is illustrated a closed loop jaw design suitable for grasping an object. The closed loop design being lockable. A further cutting jaw is illustrated in FIG. 9g. The cutting jaw in 9g having a knife edge disposable within a shallow tray. Referring to FIG. 9h, there is illustrated a deep cutting biopsy jaw. The deep cutting biopsy jaw having a tray and an opposing triangular knife blade for retaining a sample.

With the assistance of FIGS. 10a-10e, an example of a procedure for capturing an object within a patient's body cavity will be now set forth. It is understood that a multitude of cutting heads could be utilized in this context. The initial step involves passing the instrument 11 through a deployment device, such as an endoscope or a catheter, to the remote region or site in the patient. The device having been passed through the body in a retracted state to minimize exposure of the tissue to harm. Upon being placed in close proximity to the surgical site the practitioner extends the jaws to contact and provide an opening of sufficient size to accommodate the object. Once the sufficient jaw size has been obtained the practitioner manipulates the endoscope to contact the object. After contact has been established the practitioner manipulates the instrument to capture the object. After capturing the object the practitioner closes the instrument by retracting the jaws to the outer tube of the instrument or by advancing the outer tube to close the jaws.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus for performing a medical procedure, comprising:
   an elongated flexible member having a longitudinal axis and an aperture extending longitudinally therethrough, said member having a proximal end and an opposite distal end;
   an actuator positioned within said aperture, said actuator having a proximal end and an opposite distal end;
   a spring jaw connected to said distal end of said actuator, said jaw being deployable remotely for performing a medical procedure; and
   an internal jaw guide at the distal end of said member, said jaw guide having a contacting surface inclined with respect to said longitudinal axis, said jaw guide contacting along said jaw for controlling the precise movement of said jaw, said jaw guide defining a cavity within said member for receiving a substantial portion of said jaw therein.

2. The apparatus of claim 1, wherein the apparatus being deployable through a medical instrument having a lumen.

3. The apparatus of claim 2, wherein the instrument is one of a endoscope and a catheter.

4. The apparatus of claim 2, wherein said lumen having a diameter of about 4 millimeters.

5. The apparatus of claim 1, wherein said jaw includes a pair of spaced arms originating from an apex.

6. The apparatus of claim 5, wherein said spring jaw is v-shaped.

7. The apparatus of claim 6, wherein said spring jaw is formed of spring steel.

8. The apparatus of claim 5, wherein said internal jaw guide having an upper contact surface and an opposite lower contact surface, said upper and lower contact surfaces contactable with said spaced arms of said jaw.

9. The apparatus of claim 8, wherein said internal jaw guide being a slot formed in the distal end of said member.

10. The apparatus of claim 8, wherein said actuator being looped around said apex of said jaw to connect said jaw and said actuator.

11. The apparatus of claim 8, which further includes a rivet attached to said distal end of said actuator, and wherein said jaw having an aperture therethrough for the actuator to extend therethrough and said rivet retaining said actuator to said jaw.

12. The apparatus of claim 8, wherein said member is a substantially cylindrical tube, and wherein said actuator is a thin wire.

13. The apparatus of claim 12, wherein said tube has an outer diameter of about 4 mm, and wherein said wire has an outer diameter of about 0.36 mm.

14. The apparatus of claim 12, wherein said member includes a plurality of lumens extending therethrough, said plurality of lumens being isolated from one another.

15. The apparatus of claim 14, wherein said plurality of lumens includes a pair of lumens spaced 180° apart and located between said arms of said jaws.

16. The apparatus of claim 14, wherein one of said plurality of lumens is for aspirating and another of said plurality of lumens is for irrigating.

17. The apparatus of claim 14, which further includes passing electric current through one of said plurality of lumens for cauterization.

18. The apparatus of claim 5, wherein said spring jaw is formed of nitinol.

19. The apparatus of claim 1, wherein said spring jaw is a deep cutting biopsy tool.

20. The apparatus of claim 1, wherein said spring jaw is a cutting tool.

21. The apparatus of claim 1, wherein said spring jaw is a loop locking tool.

22. The apparatus of claim 1, wherein said spring jaw is a grasping jaw.

23. An apparatus for performing a medical procedure, comprising:
   an elongated flexible member having an aperture extending longitudinally therethrough, said member having a proximal end and an opposite distal end;
   an actuator positioned within said aperture, said actuator having a proximal end and an opposite distal end;
   a jaw connected to said distal end of said actuator, said jaw remotely deployable for performing a medical procedure; and
   a jaw guide at the distal end of said member, said jaw guide connecting to said member and having a pair of apertures therein for the passage of at least a portion of said jaw, said jaw guide for minimizing the lateral movement and twisting of the jaw during extension and retraction.

24. An apparatus for performing a medical procedure, comprising:
   an elongated flexible member having an aperture extending longitudinally therethrough, said member having a proximal end and an opposite distal end; an actuator positioned within said aperture, said actuator having a proximal end and an opposite distal end;
   a jaw connected to said distal end of said actuator, said jaw remotely deployable for performing a medical procedure;
   a jaw guide at the distal end of said member, said jaw guide connecting to said member and having a pair of apertures therein for the passage of at least a portion of said jaw, said jaw guide for minimizing the lateral movement and twisting of the jaw during extension and retraction; and
   wherein said jaw guide is a cap attached to said distal end of said member.

25. The apparatus of claim 24, wherein said cap is for guiding the jaws and stabilizing the distal end of said member.

26. The apparatus of claim 25, wherein the apparatus being associated with one of an endoscope and a catheter.

27. The apparatus of claim 26, wherein the apparatus being passable through an opening of about four millimeters.

28. The apparatus of claim 25, wherein said actuator being looped around said apex of said jaw to connect said jaw and said actuator.

29. The apparatus of claim 28, wherein said member is a substantially cylindrical tube, and wherein said actuator is a thin wire.

30. The apparatus of claim 29, wherein said member includes a plurality of lumens extending therethrough, said plurality of lumens being isolated from one another.

31. The apparatus of claim 30, wherein said plurality of lumens includes a pair of lumens spaced 180° apart and located between said arms of said jaw.

32. The apparatus of claim 31, wherein one of said plurality of lumens is for aspirating and another of said plurality of lumens is for irrigating.

33. An apparatus for performing a medical procedure, comprising:
   an elongated flexible member having an aperture extending longitudinally therethrough, said member having a proximal end and an opposite distal end;
   an actuator positioned within said aperture and having a proximal end and an opposite distal end, said actuator being in a close sliding fit to said aperture so as to minimize play therebetween;
   a spring jaw connected to said distal end of said actuator, said jaw deployable remotely for performing an internal medical procedure;
   an internal jaw guide at the distal end of said member, said jaw guide contacting along said jaw for controlling the precise movement of said jaw, said internal jaw guide defining a cavity within said member for receiving a substantial portion of said jaw therein; and
   a jaw guide at the distal end of said member, said jaw guide connecting to said member and having a pair of apertures therein for the passage of said jaw, said jaw guide for minimizing the lateral movement of the jaw during extension and retraction.

34. The apparatus of claim 33, wherein the apparatus being deployable through a medical instrument having a lumen.

35. The apparatus of claim 34, wherein the instrument is one of a endoscope and a catheter.

36. The apparatus of claim 34, wherein said lumen having a diameter of about 4 millimeters.

37. The apparatus of claim 34 wherein said lumen having a diameter in the range of about 1.5 millimeter to 4.0 millimeter.

38. The apparatus of claim 36, wherein said jaw includes at least a pair of spaced arms originating from an apex and said actuator being looped around said apex of said jaw to connect said jaw and said actuator.

39. The apparatus of claim 38, wherein said member includes a plurality of lumens extending therethrough, said plurality of lumens being isolated from one another.

40. The apparatus of claim 38, wherein said plurality of lumens includes a pair of lumens spaced 180° apart and located between said arms of said jaw.

41. The apparatus of claim 33, wherein said jaw being retained in said apparatus upon disconnection from said actuator.

42. The apparatus of claim 40, wherein:
   said spring jaw is v-shaped and formed of spring steel, said jaw having a pair of spaced extending arms originating from a central apex;
   said internal jaw guide contacting along a substantial portion of each of said spaced arms;
   said member being a substantially cylindrical tube;
   said actuator being a very thin wire having a outside diameter of about 0.36 millimeter; and
   one of said plurality of lumens is for aspirating contents from within the patient, and another of said plurality of lumens is for irrigating therethrough.

43. An apparatus for a medical practitioner to perform a procedure on a patient therewith, comprising:
   an elongated flexible member having an aperture extending longitudinally therethrough and having a proximal end and a opposite distal end, said member being passable through a lumen having multiple curves within the patient;
   an actuator slidable within said aperture, said actuator having a proximal end and an opposite distal end, said proximal end being external to the patient for manipulation by the practitioner;
   a spring jaw connected to said distal end of said member, said jaw being controllable remotely for performing a medical procedure; and
   wherein at least a portion of said member being deflectable and controllable upon the practitioner manipulating said proximal end of said actuator.

44. The apparatus of claim 43, wherein said lumen having an outside diameter in the range of about 1.5 millimeter to 4.0 millimeter.

45. The apparatus of claim 44, wherein said lumen having a diameter of about 4 diameter of about 4 millimeter.

46. The apparatus of claim 44, wherein:
   said jaw being substantially v-shaped and formed of a nitinol material, said jaw having a pair of spaced arms of equal length;
   said actuator looped around a portion of said jaw to connect said jaw and said actuator, said actuator being a thin wire;
   said member being a plastic substantially cylindrical tube; and
   said member further including a plurality of fluid communication lumens extending therethrough, said plurality of lumens being isolated from one another.

47. The apparatus of claim 46, which further comprises:
   an internal jaw guide at the distal end of said member, said jaw guide contacting along said jaw for controlling the precise movement of said jaw, said internal jaw guide defining a cavity within said member for receiving a substantial portion of said jaw therein; and
   a jaw guide at the distal end of said member, said jaw guide connecting to said member and having a pair of apertures therein for the passage of said jaw, said jaw guide for minimizing the lateral movement of the jaw during extension and retraction.

* * * * *